(12) United States Patent
Danielsen et al.

(10) Patent No.: US 7,267,818 B2
(45) Date of Patent: Sep. 11, 2007

(54) METHOD FOR KILLING SPORES

(75) Inventors: Steffen Danielsen, Copenhagen East (DK); Bjoern Eggert Christensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/497,732

(22) PCT Filed: Dec. 4, 2002

(86) PCT No.: PCT/DK02/00822

§ 371 (c)(1), (2), (4) Date: Jun. 4, 2004

(87) PCT Pub. No.: WO03/047351

PCT Pub. Date: Jun. 12, 2003

(65) Prior Publication Data

US 2005/0079165 A1    Apr. 14, 2005

Related U.S. Application Data

(60) Provisional application No. 60/338,282, filed on Dec. 4, 2001.

(30) Foreign Application Priority Data

Dec. 4, 2001    (DK) ............................... 2001 01799

(51) Int. Cl.
*A62D 3/00* (2006.01)
*B09B 3/00* (2006.01)
*C02F 3/34* (2006.01)
*C12N 13/00* (2006.01)
*C12M 1/00* (2006.01)
*D06M 16/00* (2006.01)

(52) U.S. Cl. .................. 424/94.4; 435/173.2; 435/262; 435/264; 435/267

(58) Field of Classification Search ..................... None
See application file for complete search history.

(56) References Cited

U.S. PATENT DOCUMENTS

| 4,937,072 A | 6/1990 | Kessler et al. |
| 6,221,821 B1 * | 4/2001 | Svendsen et al. ........... 510/226 |
| 2001/0041666 A1 * | 11/2001 | Svendsen et al. ........... 510/392 |

FOREIGN PATENT DOCUMENTS

| WO | WO95/04135 D4 | 2/1995 |
| WO | WO95/27046 D3 | 10/1995 |
| WO | WO 00/01237 D2 | 1/2000 |

* cited by examiner

*Primary Examiner*—David M. Naff
*Assistant Examiner*—Deborah K. Ware
(74) *Attorney, Agent, or Firm*—Michael W. Krenicky

(57) ABSTRACT

A method for killing or inactivating spores, by contacting the spores with a haloperoxidase, a source of hydrogen peroxide and a source of iodide ions. The spores may additionally be contacted with a haloperoxidase enhancing agent.

9 Claims, No Drawings

METHOD FOR KILLING SPORES

CROSS-REFERENCE TO RELATED APPLICATIONS

This application is a 35 U.S.C. 371 national application of PCT/DK02/00822 filed Dec. 4, 2002, which claims priority or the benefit under 35 U.S.C. 119 of Danish application no. PA 2001 01799 filed Dec. 4, 2001 and U.S. provisional application no. 60/338,282 filed Dec. 4, 2001, the contents of which are fully incorporated herein by reference.

FIELD OF THE INVENTION

The present invention relates to enzymatic methods for killing or inactivating spores.

BACKGROUND

Spores are known to form from aerobic *Bacilli*, anaerobic *Clostridia*, selected sarcinae and a few actinomycetes. Spores resemble certain plant seeds in that they do not carry out any metabolic reactions. In this regard they are especially suited to withstand severe environmental stress and are known to survive prolonged exposures to heat, drying, radiation and toxic chemicals. These properties make spores especially difficult to kill in environments, like living tissue or objects which come in contact with living tissue, which would be adversely effected by extreme conditions.

Fungi, viruses and vegetative cells of pathogenic bacteria are sterilized within minutes at 70 degrees Celsius; many spores are sterilized at 100 degrees Celsius. However, the spores of some saprophytes can survive boiling for hours. Heat is presently the most commonly used means to insure sterilization of spores.

The outer coat of spores is made of a keratin-like protein which comprises as much as 80% of the total protein of the spore. It is this protein coat which is responsible for the resistance of spores to chemical sterilizing agents. The spore stage of the microbial life cycle is characterized by metabolic dormancy and resistance to environmental factors that would destroy the microbe in its vegetative stage.

Germination of bacterial endospores and fungal spores is associated with increased metabolism and decreased resistance to heat and chemical reactants. For germination to occur, the spore must sense that the environment is adequate to support vegetation and reproduction. Simple alpha amino acids may stimulate spore germination.

The present invention provides an improved enzymatic method for killing or inactivating spores.

SUMMARY

The present invention provides a method for killing or inactivating spores, comprising contacting the spores with a haloperoxidase, a source of hydrogen peroxide and a source of iodide ions.

In an embodiment, the haloperoxidase is a chloroperoxidase or a bromoperoxidase. In another embodiment the haloperoxidase is a vanadium containing haloperoxidase.

In a yet another embodiment, the method of the invention also comprises contacting the spores with an enhancing agent which is further characterized below.

DETAILED DESCRIPTION

Haloperoxidases and Compounds Exhibiting Haloperoxidase Activity

The haloperoxidases suitable for being incorporated in the method of the invention include chloroperoxidases, bromoperoxidases and compounds exhibiting chloroperoxidase or bromoperoxidase activity. Haloperoxidases form a class of enzymes, which are capable of oxidizing halides (Cl—, Br—, I—) in the presence of hydrogen peroxide or a hydrogen peroxide generating system to the corresponding hypohalous acids according to:

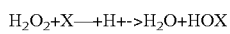

$$H_2O_2 + X^- + H^+ \rightarrow H_2O + HOX$$

wherein X— is a halide and HOX is a hypohalous acid.

Haloperoxidases are classified according to their specificity for halide ions: Chloroperoxidases (E.C. 1.11.1.10) which catalyze formation of hypochlorite from chloride ions, hypobromite from bromide ions and hypoiodite from iodide ions; and bromoperoxidases which catalyze formation of hypobromite from bromide ions and hypoiodite from iodide ions. Hypoiodite, however, undergoes spontaneous disproportionation to iodine and thus iodine is the observed product.

These hypohalite compounds may subsequently react with other compounds forming halogenated compounds.

Haloperoxidases have been isolated from various organisms: mammals, marine animals, plants, algae, lichen, fungi and bacteria. It is generally accepted that haloperoxidases are the enzymes responsible for the formation of halogenated compounds in nature, although other enzymes may be involved.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment the haloperoxidase is a vanadium haloperoxidase (i.e. a vanadium or vanadate containing haloperoxidase) derivable from *Curvularia* sp., in particular *Curvularia verruculosa* and *Curvularia inaequalis*, such as *C. inaequalis* CBS 102.42 as described in WO 95/27046, e.g. a vanadium haloperoxidase encoded by the DNA sequence of WO 95/27046, FIG. 2 all incorporated by reference; or *C. verruculosa* CBS 147.63 or *C. verruculosa* CBS 444.70 as described in WO 97/04102.

In another preferred embodiment the haloperoxidase is a vanadium containing haloperoxidase, such as a vanadium chloroperoxidase. The vanadium chloroperoxidase may be derivable from *Drechslera hartlebii* as described in WO 01/79459, *Dendiyphiella salina* as described in WO 01/79458, *Phaeotrichoconis crotalarie* as described in WO 01/79461, or *Geniculosporium* sp. as described in WO 01/79460. The vanadium haloperoxidase is more preferably derivable from *Drechslera hartlebii* (DSM 13444), *Dendryphiella salina* (DSM 13443), *Phaeotrichoconis crotalarie* (DSM 13441) or *Geniculosporium* sp. (DSM 13442).

The concentration of the haloperoxidase is typically in the range of 0.01-100 ppm enzyme protein, preferably 0.05-50 ppm enzyme protein, more preferably 0.1-20 ppm enzyme protein, and most preferably 0.5-10 ppm enzyme protein.

Determination of Haloperoxidase Activity

Microtiter assays are performed by mixing 100 µl of haloperoxidase sample (about 0.2 µg/ml) and 100 µl of 0.3 M sodium phosphate pH 7 buffer—0.5 M potassium bromide—0.008% phenol red, adding the solution to 10 µl of 0.3% $H_2O_2$, and measuring the absorption at 595 nm as a function of time.

Assays using monochlorodimedone (Sigma M4632, $\epsilon=20000$ $M^{-1}$ $cm^{-1}$ at 290 nm) as a substrate are performed as described below. The decrease in absorption at 290 nm is measured as a function of time. Assays are performed in 0.1 M sodium phosphate or 0.1 M sodium acetate, 50 µM monochlorodimedone, 10 mM KBr/KCl, and 1 mM $H_2O_2$ using a haloperoxidase concentration of about 1 µg/ml. One HU is defined as 1 micromol of monochlorodimedone chlorinated or brominated per minute at pH 5 and 30° C.

Source of Hydrogen Peroxide

The source of hydrogen peroxide required by the haloperoxidase may be hydrogen peroxide or a hydrogen peroxide precursor for in situ production of hydrogen peroxide. Any solid entity which liberates upon dissolution a peroxide which is useable by haloperoxidase can serve as the source of hydrogen peroxide. Compounds which yield hydrogen peroxide upon dissolution in water or an appropriate aqueous based medium include but are not limited to metal peroxides, percarbonates, persulphates, perphosphates, peroxyacids, alkyperoxides, acylperoxides, peroxyesters, urea peroxide, perborates and peroxycarboxylic acids or salts thereof. Any compound which generates a peroxide that haloperoxidase can use to oxidize iodides is an acceptable source of hydrogen peroxide for this invention; this includes a large number of compounds as one skilled in the art will recognize. Mixtures of two or more of these substances can also be used.

Another source of hydrogen peroxide is a hydrogen peroxide generating enzyme system, such as an oxidase together with a substrate for the oxidase. Examples of combinations of oxidase and substrate comprise, but are not limited to, amino acid oxidase (see e.g. U.S. Pat. No. 6,248,575) and a suitable amino acid, glucose oxidase (see e.g. WO 95/29996) and glucose, lactate oxidase and lactate, galactose oxidase (see e.g. WO 00/50606) and galactose, and aldose oxidase (see e.g. WO 99/31990) and a suitable aldose.

By studying EC 1.1.3._, EC 1.2.3._, EC 1.4.3._, and EC 1.5.3._or similar classes (under the International Union of Biochemistry), other examples of such combinations of oxidases and substrates are easily recognized by one skilled in the art.

The source of hydrogen peroxide may be added at the beginning of or during the process, e.g., typically in an amount corresponding to levels of from 0.001 mM to 25 mM, preferably to levels of from 0.005 mM to 5 mM, and particularly to levels of from 0.01 to 1 mM.

Source of Iodide Ions

According to the invention the source of iodide ions needed for the reaction with the haloperoxidase may be achieved in many different ways, such as by adding a salt of iodide. In a preferred embodiment the salt of iodide is sodium iodide or potassium iodide, or a mixture thereof.

The concentration of the source of iodide ions will typically correspond to a concentration of iodide ions of from 0.01 mM to 1000 mM, preferably in the range of from 0.05 mM to 500 mM.

Enhancing Agent

We have observed that an improved antimicrobial activity may be obtained by including an enhancing agent in the composition of the invention. Preferably the enhancing agent is an amine compound, which may be a compound of the following formula:

wherein the substituent groups R1 and R2, which may be identical or different, represent any of the following radicals: hydrogen, phenyl, and $C_{1-6}$-alkyl;

which phenyl and $C_{1-6}$-alkyl groups may be unsubstituted or substituted with one or more independent substituent groups R3;

which substituent group R3 represents any of the following radicals: hydroxy, halogen, formyl, carboxy and esters and salts thereof, carbamoyl, sulfo and esters and salts thereof, sulfamoyl, nitro, amino, phenyl, acyl, $C_{1-6}$-alkyl, and $C_{1-6}$-alkoxy;

which carbamoyl, sulfamoyl, amino, phenyl, $C_{1-6}$-alkyl, $C_{1-6}$-alkoxy and acyl groups may furthermore be unsubstituted or substituted with one or more independent substituent groups R4;

which substituent group R4 represents any of the following radicals: halogen, hydroxy, formyl, carboxy and esters and salts thereof, carbamoyl, sulfo and esters and salts thereof, sulfamoyl, nitro, amino, phenyl, acyl, $C_{1-6}$-alkyl, and $C_{1-6}$-alkoxy;

which carbamoyl, sulfamoyl, and amino groups may furthermore be unsubstituted or substituted independently once or twice with hydroxy, $C_{1-4}$-alkyl and $C_{1-4}$-alkoxy; and which phenyl, $C_{1-6}$-alkyl, $C_{1-6}$-alkoxy and acyl groups may furthermore be unsubstituted or substituted independently with one or more of the following groups: halogen, hydroxy, amino, formyl, carboxy and esters and salts thereof, carbamoyl, sulfo and esters and salts thereof, and sulfamoyl.

In an embodiment, when the substituent group R3 is a carboxy group or an ester thereof, R3 cannot be directly connected to a carbon atom which is directly connected to the nitrogen atom in the above formula.

The term "$C_{1-n}$-alkyl" wherein n can be from 2 through 6, as used herein, represents a saturated or unsaturated, and branched or straight alkyl group having from one to the specified number of carbon atoms (n). Typical $C_{1-6}$-alkyl groups include, but are not limited to, methyl, ethyl, ethenyl (vinyl), n-propyl, isopropyl, propenyl, isopropenyl, butyl, isobutyl, sec-butyl, tertbutyl, crotyl, methallyl, pentyl, isopentyl, propenyl, prenyl, hexyl, isohexyl, and the like.

The term "$C_{1-n}$-alkoxy" wherein n can be from 2 through 6, as used herein, represents a $C_{1-n}$-alkyl group linked through an ether group; such as methoxy, ethoxy, propoxy, isopropoxy, butoxy, isobutoxy, sec-butoxy, tert-butoxy, pentoxy, and the like.

The term "acyl" as used herein refers to a monovalent substituent comprising a $C_{1-6}$-alkyl group linked through a carbonyl group; such as acetyl, propionyl, butyryl, isobutyryl, pivaloyl, valeryl, and the like.

As used herein, the amine compounds may be in their cationic form.

In an embodiment the enhancing agent is not an alpha amino acid.

In a preferred embodiment R1 is hydrogen.

In another preferred embodiment R1 is hydrogen and R2 is an alcohol (amino alcohol), e.g., ethanolamine.

In a further preferred embodiment the amine compound is an ammonium salt, i.e. any ammonium salt known in the art: e.g., diammonium sulphate, ammonium chloride, ammonium bromide, or ammonium iodide.

The enhancing agent may be present in the composition in a concentration in the range of from 0.01 mM to 1000 mM, preferably in the range of from 0.05 mM to 500 mM, more preferably in the range of from 0.1 mM to 100 mM, and most preferably in the range of from 0.1 mM to 50 mM.

Spores

The spores which are contacted with a haloperoxidase, a source of hydrogen peroxide and a source of iodide ions in the method of the invention comprise all kinds of spores.

In an embodiment the spores are endospores, such as all *Clostridium* sp. spores, *Brevibacillus* sp. spores and *Bacillus* sp. spores, e.g. spores from *Bacillus anthracis, Bacillus cereus, Bacillus subtilis, Bacillus putida*, and *Bacillus pumila*.

In another embodiment the spores are exospores, such as *Actinomycetales* spores, e.g. spores from *Actinomyces* sp., *Streptomyces* sp., *Thermoactinomyces* sp., *Saccharomonospora* sp., and *Saccharopylospora* sp.

In another embodiment the spores are bacterial spores. Examples of bacterial spores include, but are not limited to, all *Clostridium* sp. spores and *Bacillus* sp. spores as mentioned above.

In yet another embodiment the spores are fungal spores. Examples of fungal spores include, but are not limited to, conidiospores, such as spores from *Aspergillus* sp., and *Penicillium* sp.

Methods and Uses

The present invention provides a composition, comprising a haloperoxidase, a source of hydrogen peroxide and a source of iodide ions.

The present invention also provides an enzymatic method for killing or inactivating spores, comprising contacting the spores with a haloperoxidase, a source of hydrogen peroxide and a source of iodide ions.

The haloperoxidase, the source of hydrogen peroxide and the source of iodide ions may be formulated as a liquid (e.g. aqueous) or a dry product formulation. The dry product formulation may subsequently be re-hydrated to form an active liquid or semi-liquid formulation usable in the method of the invention.

When the haloperoxidase, the source of hydrogen peroxide and the source of iodide ions are formulated as a dry formulation, the components may be mixed, arranged in discrete layers or packed separately.

In an embodiment, the method of the invention does not comprise contacting the spores with an alpha amino acid.

The method of the invention is useful for decontamination of locations which have been exposed to spores, such as biological warfare agents, e.g. spores of *Bacillus anthracis* capable of causing anthrax.

In the context of the present invention the term "killing or inactivating spores" is intended to mean that at least 99% of the spores are not capable of transforming (germinating) into vegetative cells. Preferably 99.9% (more preferably 99.99% and most preferably 99.999%) of the spores are not capable of transforming into vegetative cells.

The spores may be contacted by the composition of the invention at a temperature between 0 and 90 degrees Celsius, preferably between 5 and 80 degrees Celsius, more preferably between 10 and 70 degrees Celsius, even more preferably between 15 and 60 degrees Celsius, most preferably between 18 and 50 degrees Celsius, and in particular between 20 and 40 degrees Celsius.

The composition of the invention is suitable for killing or inactivating spores in a variety of environments. The composition of the invention may desirably be used in any environment to reduce spore contamination, such as the health-care industry (e.g. animal hospitals, human hospitals, animal clinics, human clinics, nursing homes, day-care facilities for children or senior citizens, etc.), the food industry (e.g. restaurants, food-processing plants, food-storage plants, grocery stores, etc.), the hospitality industry (e.g. hotels, motels, resorts, cruise ships, etc.), the education industry (e.g. schools and universities), etc.

The composition of the invention may desirably be used in any environment to reduce spore contamination, such as general-premise surfaces (e.g. floors, walls, ceilings, exterior of furniture, etc.), specific-equipment surfaces (e.g. hard surfaces, manufacturing equipment, processing equipment, etc.), textiles (e.g. cottons, wools, silks, synthetic fabrics such as polyesters, polyolefins, and acrylics, fiber blends such as cottonpolyester, etc.), wood and cellulose-based systems (e.g. paper), soil, animal carcasses (e.g. hide, meat, hair, feathers, etc.), foodstuffs (e.g. fruits, vegetables, nuts, meats, etc.), and water.

In one embodiment, the method of the invention is directed to sporocidal treatment of textiles. Spores of the *Bacillus cereus* group have been identified as the predominant postlaundering contaminant of textiles. Thus, the treatment of textiles with a composition of the invention is particularly useful for sporocidal activity against the contaminants of textiles. Examples of textiles that can be treated with the composition of the invention include, but are not limited to, personal items (e.g. shirts, pants, stockings, undergarments, etc.), institutional items (e.g. towels, lab coats, gowns, aprons, etc.), hospitality items (e.g. towels, napkins, tablecloths, etc.).

A sporocidal treatment of textiles with a composition of the invention may include contacting a textile with a composition of the invention. This contacting can occur prior to laundering the textile. Alternatively, this contacting can occur during laundering of the textile to provide sporocidal activity and optionally provide cleansing activity to remove or reduce soils, stains, etc. from the textile.

The spores which are contacted by the composition of the invention may be situated on any surface including, but not limited to, a surface of a process equipment used in e.g. a dairy, a chemical or pharmaceutical process plant, a piece of laboratory equipment, a water sanitation system, an oil processing plant, a paper pulp processing plant, a water treatment plant, or a cooling tower. The composition of the invention should be used in an amount, which is effective for killing or inactivating the spores on the surface in question.

The spores may be contacted with the composition of the invention by submerging the spores in an aqueous formulation of the composition (e.g. a laundering process), by spraying the composition onto the spores, by applying the composition to the spores by means of a cloth, or by any other method recognized by the skilled person. Any method of applying the composition of the invention to the spores, which results in killing or inactivating the spores, is an acceptable method of application.

The method of the invention is also useful for decontamination of locations which have been exposed to spores (e.g. pathogenic spores), such as biological warfare agents, e.g. spores of *Bacillus anthrasis* capable of causing anthrax. Such locations include, but are not limited to, clothings (such as army clothings), inner and outer parts of vehicles, inner and outer parts of buildings, any kind of army facility, and any kind of environment mentioned above.

The present invention is further described by the following examples which should not be construed as limiting the scope of the invention.

EXAMPLES

Chemicals used as buffers and substrates were commercial products of at least reagent grade.

Example 1

Spore Production

Streak a Tryptose Blod Agar Base (TBAB) plate from a fresh culture of *Bacillus globigli* or *B. thuringiensis* (*Bacillus thuringiensis* type strain ATCC10792). Incubate the culture overnight at 30 degrees Celsius.

Suspend a loopfull of pure *Bacillus* from the TBAB plate and suspend the cells in 2 ml of sterile water. Inoculate 2×SG plates with 100 µl of the cell suspension on each. The composition of 2×SG is as follows: 16 g/L Difco Bacto Nutrient Broth, 0.5 g/L $MgSO_4 \times 7H_2O$, 2.0 g/L KCl, 1.0 ml/100 ml of 10% glucose, 0.1 ml/100 ml of 1 M $Ca(NO_3)_2$, 0.1 ml/100 ml of 0.1 M $MnSO_4$, 10 µl/100 ml of 0.01M $FeSO_4$, and 1% Difco Bacto Agar.

Incubate plates for 48-72 hrs. at 30 degrees Celsius. Check for sporulation with phase-contrast microscopy. Spores are phase-bright.

When sporulation efficiency is close to 100%, harvest the cell lawn with water and suspend the cells by intensive vortexing. Collect cells by centrifugation for 5-10 minutes at 6000G at 4 degrees Celsius. Wash cells 3× with ice cold water. The pellet contains vegetative cells and spores.

Apply a step-density gradient for separation of the spores from the vegetative cells. Prepare for each washed pellet a centrifuge tube containing 30 ml 43% Urographin®. Prepare 3 ml of cell spore mixture in Urographin so that the final Urographin concentration is 20%. Gently load the 20% Urographin cell/spore mixture onto the top layer of the 43% Urographin. Centrifuge at 10000G at room temperature for 30 minutes. Gently remove supernatant. Suspend the pure spore pellet in 1 ml ice-cold water and transfer to a microfuge tube. Centrifuge at maximum speed for 1-2 min at 4 degrees Celsius, wash pellet in ice-cold water 2 more times.

Check purity and number of spores/ml by phase contrast microscopy and a haemocytometer. Store spores suspended in water at −20 degrees Celsius.

Example 2

Killing of *Bacillus* Spores in Liquid Preparations $10^6$ Spores of *Bacillus globigli* were seeded in wells A1-A6 in a microtiter dish and $10^6$ spores of *Bacillus thuringiensis* spores in wells A7-A12.

In wells A1-A3 and A7-A9 were added the haloperoxidase killing system to a final concentration of 1 mM $H_2O_2$, 1 mM KI, 1 mg/L *Curvularia verruculosa* Haloperoxidase (referred to as HPO) in DMG buffer (50 mM DMG, pH 6.0). Total volume in wells was 250 µL. In wells A4-A6 and A10-A12 were added DMG buffer (50 mM DMG, pH 6.0) to a total volume of 250 µL.

The microtiter plate was incubated for 60 minutes at 30 degrees Celsius, and the contents serially diluted, columnwise, in 10-fold steps into TBB medium (Tryptose Blod Agar Base w/o agar). The plates were then incubated overnight at 30 degrees Celsius in a moist chamber. Growth in the dilution series was scored after 18-24 hours either by reading OD620 with a plate reader or by visually inspecting the plates after addition of 5 µL of 3 mM MTT/well. MTT is a tetrazolium dye which forms a purple unsoluble formazan dye when living cells are present. Comparison of wells for living/dead cells, directly gives the killing effect in log Units. For *Bacillus globigli* the kill was determined to 5 log units and for *Bacillus thuringiensis* the kill was determined to 6 log units.

Example 3

Kill Rates for Spores Suspended in Liquid HPO-KI for Increasing Amounts of Haloperoxidase and KI Using the system described in example 1 and 2 *Bacillus globigli* spores were treated with haloperoxidase (HPO)+KI (both in increasing concentrations)+1 mM $H_2O_2$ in 50 mM DMG buffer, pH 6.0. Following 60 minutes incubation at room temperature, sterile filtered $Na_2S_2O_3$, (which quenches $I_2$) to a final concentration of 1%. Subsequent serial dilutions in TBB growth medium revealed the number of spores killed.

TABLE 1

Results from dose-response kill experiments with *Bacillus globigii* spores in HPO-KI liquid.

| | HPO, conc. | | | | | |
|---|---|---|---|---|---|---|
| | 1 mg/L | | 5 mg/L | | | |
| | KI, conc. | | | | | |
| | 1 mM | 5 mM | 1 mM | 10 mM | 50 mM | 100 mM |
| Kill | ~5 log U | ~3 log U | 2 log U | 0–1 log U | 0–1 log U | 0–1 log U |

Example 4

Temperature Dependent Spore Killing

*Bacillus globigli* and *Bacillus thuringiensis* spores were subjected to the action of haloperoxidase+KI+$H_2O_2$ for 1 hour at 10° C., 15° C., 20° C., 25° C., 30° C., 35° C., 40° C., 45° C., 50° C., 55° C. and 60° C.

To *Bacillus globigli* spores ($10^7$/microfuge tube) and *Bacillus thuringiensis* spores ($10^5$/microfuge tube) was added 1 ml of the germicidal mixture described in Example 2. The tubes were allowed to incubate at the relevant temperature for 60 minutes in a water-bath. Spores suspended in 1 ml 50 mM DMG buffer pH 6.0 acted as controls. At the end of the heat treatment a dilution series (10-fold dilutions) was made in sterile water and aliquots from the dilutions plated onto Tryptose Blod Agar Base. The plates were incubated over night at 30° C. By scoring CFU the killing effect of the germicidal system at various temperatures was calculated. The results are given in log units.

TABLE 2

| | Kill, scored in log units. | | | | | | | | | | |
|---|---|---|---|---|---|---|---|---|---|---|---|
| | 10° C. | 15° C. | 20° C. | 25° C. | 30° C. | 35° C. | 40° C. | 45° C. | 50° C. | 55° C. | 60° C. |
| Bacillus globigii | 0.5 | 1 | 2 | 3 | 4 | 5 | 6 | 7 | 7 | 6 | 7 |
| Bacillus thuringiensis | 2 | 4 | 5 | 5 | 5 | 5 | 5 | 5 | 5 | 5 | 5 |

Example 5

Application of the Haloperoxidase-KI System to Surfaces

Dosage-response experiments demonstrate that increased concentrations of enzyme and KI and thus free $I_2$ increase the killing effect on ceramic surfaces.

Tiles were sprayed with a suspension of *Bacillus globigli* spores (approx. $10^6$ spores/ml) in water, allowed to dry completely and then sprayed with the following mixture: Haloperoxidase+KI+1 mM $H_2O_2$ in 50 mM DMG buffer pH 6.0. Following 60 minutes incubation in a moist chamber excess fluid was allowed to evaporate at room temperature and the tiles were covered with TBB nutrient medium solidified with 0.5% agarose. Incubated at 30° C. in a moist chamber over night, the developing microcolonies were visualized my applying 1 mM MTT, which forms a purple formazan when in contact with respiring organisms. By counting microcolonies on HPO/$I_2$ treated and untreated control tiles, the degree of kill was calculated.

TABLE 3

Kill rates of varying HPO-KI concentrations on *Bacillus* spores on ceramic tiles.

| | HPO conc. | | | | |
|---|---|---|---|---|---|
| | 1 mg/L | 5 mg/L | 10 mg/l | 10 mg/l | 10 mg/L |
| | | | KI conc. | | |
| | 1 mM | 1 mM | 1 mM | 5 mM | 10 mM |
| Kill | 1–2 log U | 1–2 log U | 1–2 log U | ~2 log U | ~3 log U |

Example 6

Using the method of Example 5, the effect of HPO was combined with that of Glucose oxidase (GOX), which in the presence of glucose and oxygen forms hydrogen peroxide. Ceramic tiles (reverse side) inoculated with *Bacillus globigli* spores, approx. 3×10E6/tile, were covered with decontamination fluid consisting of 5 mg/l *Curvularia verruculosa* haloperoxidase (rCvP), 2 mg/L glucose oxidase (GOX), 1% (w/v) glucose, 5 mM KI, 1 mM $H_2O_2$, 0.2%(w/v) *Quillaja saponin*, 0.3% methyl cellulose, 100 mM Tris buffer pH 6.5, or with the rCvP-KI system alone, or the GOX-glucose system alone. Buffer+methyl cellulose+saponin was used as control. After the decontamination procedure, the tiles were allowed to dry at room temperature for 24 hours. The tiles were then coated with a nutrient agarose and incubated for 20 hours at 34° C. Subsequently microcolonies were visualized by applying 1 mM MTT, a dye which detect live cells, to the surface of the agarose. By determining the area density of microcolonies on the tiles the decontamination effect was assessed.

TABLE 4

Kill rates, in log Units, of HPO, HPO + GOX and GOX enzyme preparations on spores on a ceramic surface.

| | HPO | HPO + GOX | GOX |
|---|---|---|---|
| B. globigii | 2 | 5 | 3–4 |
| B. thuringiensis | 2 | 5–6 | 3–4 |

Example 7

Application of the Haloperoxidase-KI System to Terry Cloth Pieces

Cloth pieces (5 cm×5 cm) were inoculated with *Bacillus globigli* spores allowed to dry, soaked with 5 mg/L haloperoxidase, 5 mM KI, 1 mM $H_2O_2$ in 50 mM DMG buffer pH 6.0 and incubated for 60 minutes. Then $Na_2S_2O_3$, quenching the $I_2$ action, was added to a final concentration of 1% (w/v) and allowed to react for 30 minutes. The non-quenched samples were treated with sterile water. Following quenching, the cloth pieces were put into 25 ml centrifuge tubes, covered with sterile water and incubated on a circular shaker (300 rpm) for approx. 20 hrs at 4° C. Plating diluted samples onto TBAB and counting the emerging bacterial colonies, determined live spores in the washing water. Approximately ⅓ of the spores seeded onto the cloth were liberated and could consequently be detected in the 'washing liquid'.

TABLE 5

The killing effect of the haloperoxidase-KI system on terry cloth pieces.

| | HPO-KI w/o quenching | | HPO-KI with quenching | |
|---|---|---|---|---|
| | 20° C. | 30° C. | 20° C. | 30° C. |
| Kill, log U | 1 | 1 | 0 | 0.5 |

Example 8

Decontamination of Flannel Cloth Pieces

Flannel cloth pieces 1.2 cm×1.2 cm were inoculated with approximately 10E8 *Bacillus thuringiensis* spores in water. The cloth was allowed to dry overnight at room temperature. Two ml of decontamination fluid, consisting of 100 mM DMG buffer pH 6.0 containing 0.2% *Quillaja saponin*, 0.3% methyl cellulose, 1 mM $H_2O_2$, 5 mM KI, haloperoxidase (HPO) (see concentrations in table 6) and in combination with 1% glucose and 2 mg/L glucose oxidase (GOX) was applied to the cloth pieces and incubated (in 4.5 cm ø open petri dishes), at room temperature for approximately 18-20 hours. At that time the cloth pieces (now dry) were placed in wide 30 ml centrifuge tubes and covered with 10 ml sterile 0.1% Tween. The tubes were placed in an ultrasonic cleaning bath (Branson) and treated for 60 minutes. Then 100 μL of the now spore enriched fluid was transferred to wells in the A row in a microtiter dish and 10-fold dilutions, column-wise, as described in Example 2, were done. The microtiter-dish was incubated over-night in a moist chamber at 30 degrees Celsius and growth was scored as described in Example 2. Results are shown in table 6.

TABLE 6

Decontamination of flannel cloth pieces.

|  | Untreated | 1 mg/L HPO | 1 mg/L HPO + GOX | 5 mg/L HPO | 5 mg/L HPO + GOX | 10 mg/L HPO | 10 mg/L HPO + GOX |
| --- | --- | --- | --- | --- | --- | --- | --- |
| Kill, Log U | 0 | 0.5 | 2.5 | 4.5 | 5 | 6 | 6 |

The invention claimed is:

1. An enzymatic method for killing or inactivating spores, which comprises contacting the spores with a surfactant, a haloperoxidase, a source of hydrogen peroxide and a source of iodide ions, wherein the haloperoxidase is a vanadium containing chloroperoxidase or bromoperoxide.

2. The method of claim 1, wherein the source of iodide ions is a salt of iodide.

3. The method of claim 1, which further comprises contacting the spores with an antimicrobial enhancing agent.

4. The method of claim 1, wherein the spores are located on a surface.

5. The method of claim 4, wherein the surface is a textile surface.

6. The method of claim 4, wherein the surface is a surface of laboratory or process equipment.

7. A method of decontaminating a location exposed to spores, which comprises contacting the spores with a haloperoxidase, a source of hydrogen peroxide, a source of iodide ions and an antimicrobial enhancing agent, wherein the haloperoxidase is a vanadium containing chloroperoxidase or bromoperoxidase.

8. The method of claim 7, wherein the source of iodide ions is one or more salts of iodide.

9. A container comprising a vanadium containing chloroperoxidase or bromoperoxidase, a source of hydrogen peroxide and a source of iodide ions, wherein the chloroperoxidase or bromoperoxidase, the source of hydrogen peroxide and the source of iodide ions are packaged in one or more compartments or layers.

* * * * *